(12) United States Patent
Wee

(10) Patent No.: US 7,469,188 B2
(45) Date of Patent: Dec. 23, 2008

(54) METHOD AND FLOW METER FOR DETERMINING THE FLOW RATE OF A MULTIPHASE FLUID

(75) Inventor: Arnstein Wee, Oslo (NO)

(73) Assignee: Multi Phase Meters AS, Stavanger (NO)

( * ) Notice: Subject to any disclaimer, the term of this patent is extended or adjusted under 35 U.S.C. 154(b) by 52 days.

(21) Appl. No.: 10/582,532

(22) PCT Filed: Dec. 9, 2004

(86) PCT No.: PCT/NO2004/000379

§ 371 (c)(1),
(2), (4) Date: Aug. 18, 2006

(87) PCT Pub. No.: WO2005/057142

PCT Pub. Date: Jun. 23, 2005

(65) Prior Publication Data

US 2007/0124091 A1 May 31, 2007

(30) Foreign Application Priority Data

Dec. 9, 2003 (NO) ................................. 20035481

(51) Int. Cl.
*G01F 1/00* (2006.01)
*G06F 17/00* (2006.01)
(52) U.S. Cl. ............................ 702/45; 702/50; 702/49; 702/100; 73/861.01
(58) Field of Classification Search ................... 702/45, 702/50, 100
See application file for complete search history.

(56) References Cited

U.S. PATENT DOCUMENTS

| 4,458,524 A | 7/1984 | Meador et al. ............. 73/61.43 |
| 4,829,831 A | 5/1989 | Kefer et al. |
| 5,103,181 A | 4/1992 | Gaisford et al. ............. 324/637 |
| 5,135,684 A | 8/1992 | Mohn et al. .................... 261/76 |

(Continued)

FOREIGN PATENT DOCUMENTS

EP 0 510 774 10/1992

(Continued)

OTHER PUBLICATIONS

International Search Report dated May 9, 2005.

(Continued)

*Primary Examiner*—Hal D Wachsman
(74) *Attorney, Agent, or Firm*—Nields & Lemack

(57) ABSTRACT

Method and apparatus for determining the flow rates and/or composition of a fluid comprising a multi-component mixture of a gas and at least one liquid in a pipe. Electromagnetic loss and phase measurements are performed in at least two directions of the pipe; the degree of annular flow is determined based on these measurements; the permittivity of the flow mixture is calculated, including corrections for the degree of annular flow; the mixture density is measured and compensated for the degree of annular flow; the temperature and pressure are obtained; the velocity of liquid and gas are determined, and based on the knowledge of densities and permittivities of the components of the fluid mixture, and the result from the above steps, the volume and mass flow rates of the gas and liquid(s) of the fluid mixture are calculated.

21 Claims, 9 Drawing Sheets

U.S. PATENT DOCUMENTS

| | | |
|---|---|---|
| 5,367,911 A | 11/1994 | Jewell et al. |
| 5,485,743 A * | 1/1996 | Taherian et al. ............. 73/61.44 |
| 5,929,342 A * | 7/1999 | Thompson ............... 73/861.04 |
| RE36,597 E | 3/2000 | Agar et al. ............... 73/861.04 |
| 6,097,786 A | 8/2000 | Groves et al. ................. 378/53 |
| 6,272,934 B1 | 8/2001 | Rajan et al. |
| 6,332,111 B1 * | 12/2001 | Fincke ......................... 702/50 |
| 6,335,959 B1 * | 1/2002 | Lynch et al. ................. 378/45 |
| 6,405,604 B1 | 6/2002 | Berard et al. |
| 6,466,035 B1 * | 10/2002 | Nyfors et al. ............... 324/634 |
| 6,601,458 B1 * | 8/2003 | Gysling et al. ........... 73/861.04 |
| 6,655,221 B1 | 12/2003 | Aspelund et al. |
| 6,813,962 B2 * | 11/2004 | Gysling et al. ........... 73/861.26 |
| 2004/0244501 A1 * | 12/2004 | Nyfors et al. ............ 73/861.63 |

FOREIGN PATENT DOCUMENTS

| | | |
|---|---|---|
| GB | 2313445 | 11/1997 |
| GB | 2330660 | 4/1999 |
| WO | 90/02940 | 3/1990 |
| WO | 90/02941 | 3/1990 |
| WO | 00/45133 | 8/2000 |
| WO | 03/034051 | 4/2003 |

OTHER PUBLICATIONS

International Search Report dated May 22, 2000.

* cited by examiner

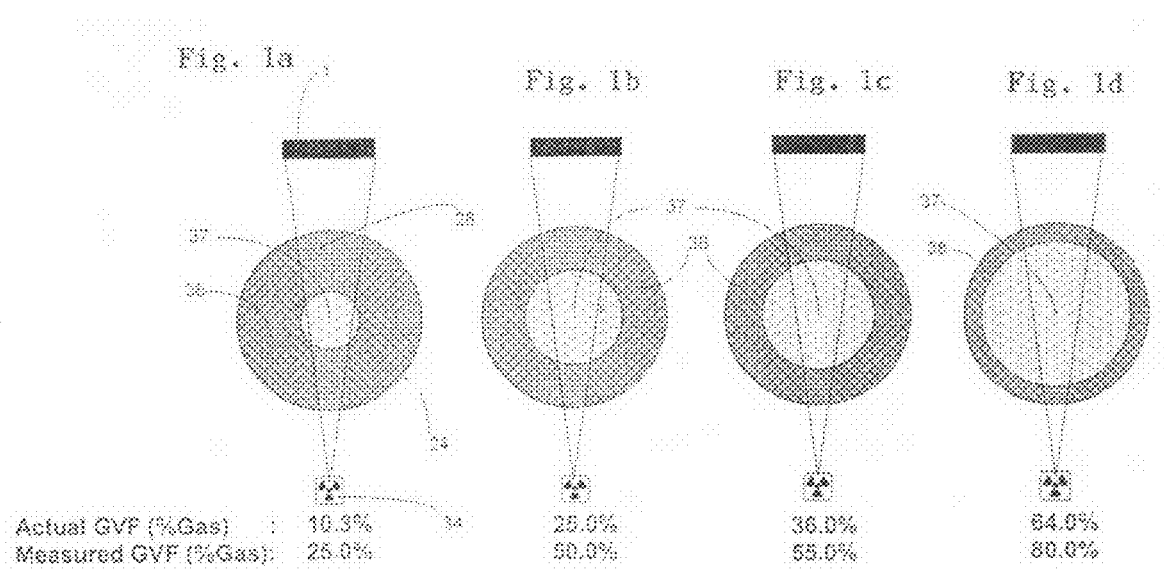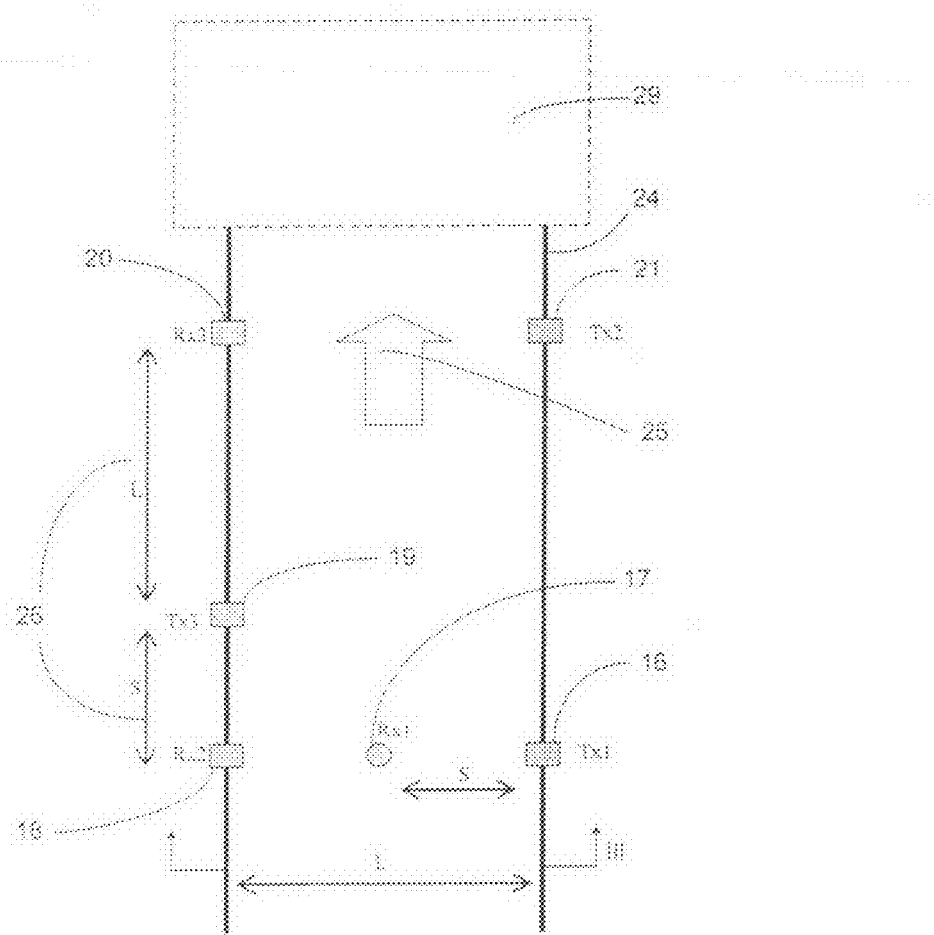

Fig 5
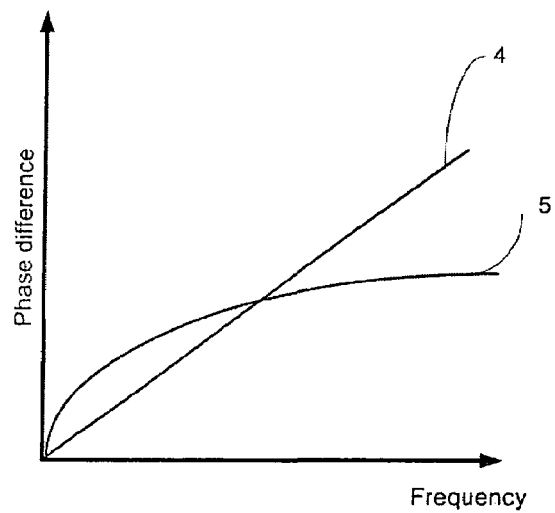
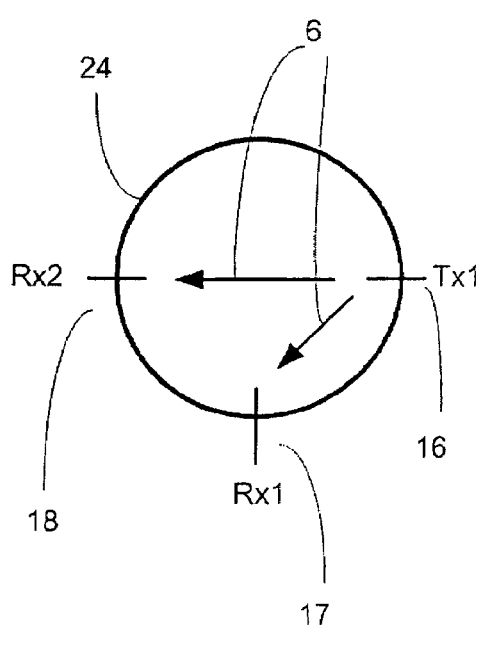
Fig. 6a
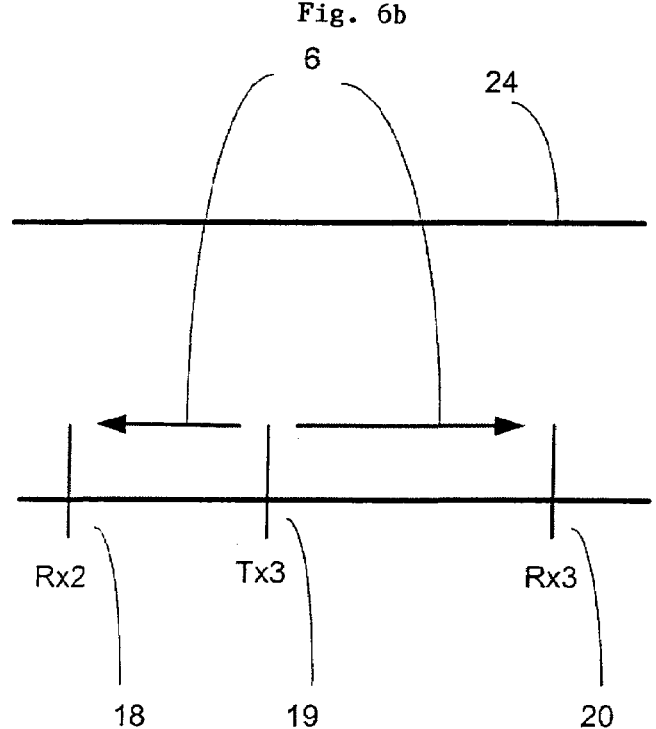
Fig. 6b

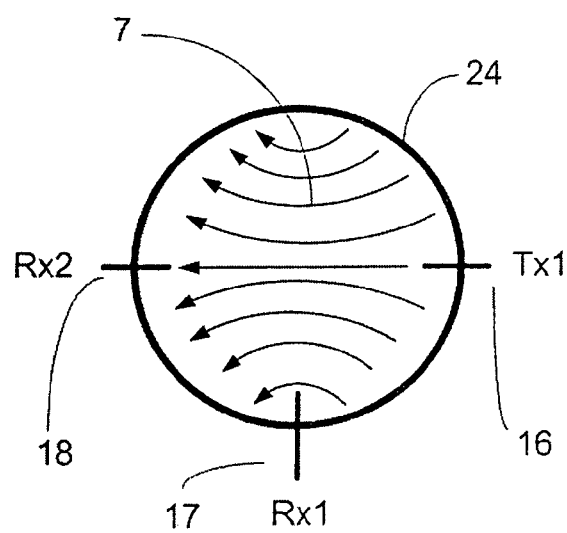
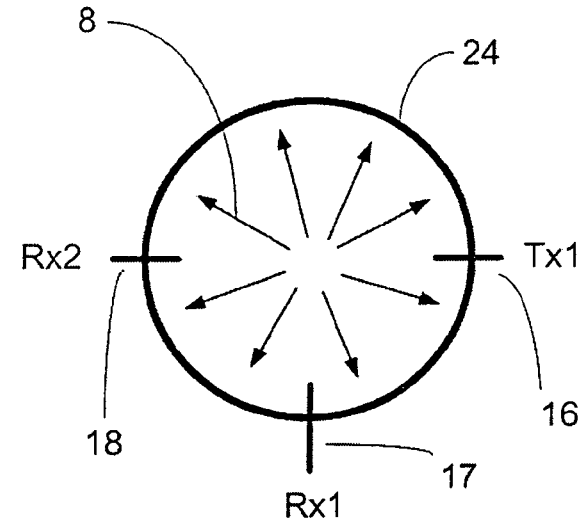
Fig. 8
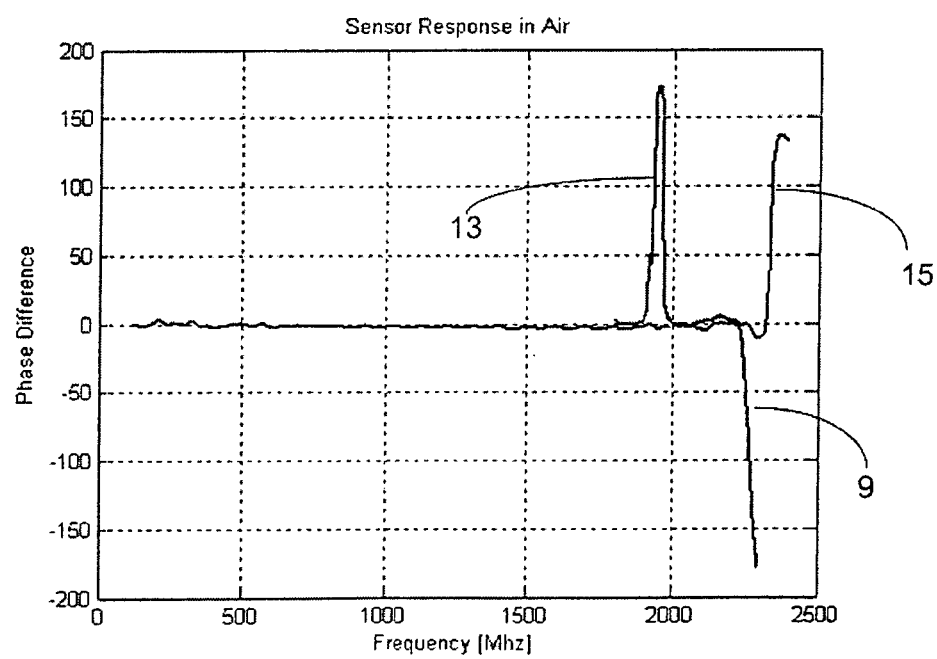

METHOD AND FLOW METER FOR DETERMINING THE FLOW RATE OF A MULTIPHASE FLUID

This application is a §371 of PCT/NO04/00379 filed on Dec. 9, 2004, which claims priority of Norwegian Patent Application No. 20035481 filed on Dec. 9, 2003.

The present invention relates to a method and flow meter for determining the composition and flow rates of individual components of a multiphase fluid, as defined in the preambles of certain claims.

The problem of how to meter oil-water-gas mixtures has been of interest to the petroleum industry since the early 1980s. Since then considerable research has been conducted into the development of a three-phase flow meter suitable for use in an industrial environment.

There are several techniques and known instruments for measuring multiphase flow, as will be further described below. Such instruments need to be reasonably accurate (typically ±5% of rate for each phase), non-intrusive, reliable, flow regime independent, and suitable for use over the full component fraction range. In spite of the large number of solutions that have been proposed in recent years, no commercially available three phase flow meter yet meets all these requirements.

The output of an oil/gas reservoir may vary greatly, depending on the location and age of the well. In addition to the oil and gas components, water, sand and wax may also be present in the produced well stream. Since the location and output of a well may vary so widely, the systems that have been designed to collect and process this output also vary considerably. The initial target of the oil industry to develop a universal multiphase flow meter to replace the traditional separation/single phase metering solution currently used, the fiscal monitoring of a well's output, have yet to be realised.

Multiphase flow meters are increasingly used for well testing and allocation measurement. In order to optimise the production and life of an oil/gas field, operators need to be able to regularly monitor the output of each well in the field. The conventional way of doing this is to use a test separator. Test separators are expensive, occupy valuable space on a production platform, and require a long time to monitor each well because of the stabilised flow conditions required. In addition, test separators are only moderately accurate (typically ±5 to 10% of each phase flow rate) and cannot be used for continuous well monitoring. A three-phase flow meter could be used in the first instance instead of a test separator and in the long term as a permanent installation on each well. Such an arrangement would save the loss in production normally associated with well testing. Such loss is estimated to be approximately 2% for a typical offshore installation. Allocation metering is needed when a common pipeline is used to transport the output from a number of wells owned by different companies to a processing facility. This is currently achieved by passing the output of each well through a test separator before entering the common pipeline. However, in addition to the disadvantages of the test separator described above, dedicated test pipelines to each well are also required. A permanently installed three-phase flow meter would offer significant advantages for allocation metering.

According to a group of major oil companies, the accuracy requirements for a multiphase meter within a gas volume fraction range of 0-99% and water cut range of 0-90%, is 5-10% relative error on the liquid and gas flow rate and water cut measurement error within 2% abs. More accurate measurements were required for production allocation applications. Commercial three-phase flow meters are now generally capable of measuring individual phase fraction's flow rate to an uncertainty of less than 10% over a reasonably wide range of flow rates and phase fractions. There are two areas of operation which need further investigation if flow rate uncertainty is to be reduced still further using current combinational measurement techniques: flow regime dependency and individual phase velocity measurement.

The present invention aims at providing a method and means which significantly reduce this uncertainty, particularly the uncertainty related to flow regime dependency.

Some examples of commercially available non-intrusive multiphase meters such as those known from NO 304333, NO 304332, U.S. Pat. No. 5,103,181, WO 00/45133 (FIG. 5) and U.S. Pat. No. 6,097,786, measure the cross sectional composition and velocity of the phases to obtain flow rates. In order to provide accurate measurements, a homogeneous mixture in the cross section of the pipe is required. Effects due to inhomogenity in the longitudinal direction of the pipe is normally minimised by fast sampling of the cross-sectional composition. Multiphase meters are normally not mounted in a horizontal position due to the presence of laminar flow, where water is in the bottom of the pipe and gas at the top, which would distort the measurement. Consequently, to achieve homogeneous mixture in the cross section of the pipe of a multiphase meter, it is common practice to install the multiphase meters in such a way that the flow is flowing in an upward or downward direction. Laminar flow may then be avoided. However, when a multiphase mixture containing gas and liquid(s) are flowing in a vertical direction, annular flow can occur. Annular flow means that most of the liquid is distributed as a ring along the walls of the pipe and most of the gas is concentrated in the middle of the pipe. Annular flow distorts the measurement in a similar manner as laminar flow in a horizontal installation. In horizontal pipes pure annular flow where all the gas is in the middle of the pipe would normally only occur at higher gas fractions. However, when the flow is flowing in vertical pipes, severe concentration of gas in the middle of the pipe has been experienced even at medium flow rates (a few m/s) and gas fractions as low as 10%. Even a concentration of the gas in the middle of the pipe at lower gas fractions would introduce severe measurement errors. In practice, the liquid is rarely completely free of gas. In the context of this patent application, we define the degree of annular flow as, one minus the amount of free gas at the pipe wall divided by the amount of free gas in the middle of the pipe, as shown in the equation below.

$$DOAF = 1 - \frac{GVF_W}{GVF_C}$$

Where
DOAF=Degree of Annular Flow
$GVF_W$=The amount of free gas at the pipe wall
$GVF_C$=The amount of free gas in the middle of the pipe In other words, for a degree of annular flow of 1.0 (or 100%), all the gas volume is located in the middle of the pipe and all the liquid volume is distributed as a ring along the wall. Furthermore, for a degree of annular flow of 0 (or 0%), the gas volume is evenly distributed throughout the entire cross section of the pipe. Furthermore, for a degree of annular flow of 0.5 (or 50%), there is twice as much gas volume in the middle of the pipe compared to the gas volume at the pipe wall. The values $GVF_W$ and $GVF_C$ are in the present invention only used in connection with calibration of the mathematical model describing the relationship between the measured data and the degree of annular flow and not a direct part of the equations for calculation of the flow rates.

NO 304333, U.S. Pat. Nos. 5,103,181, 6,097,786 and 5,135,684 uses a nuclear densitometer. When a nuclear densitometer is used to measure the density, it is not possible to obtain full coverage of the cross section of the pipe. Hence, in order to obtain accurate measurements, it relies on a homogeneous mixture in the cross section. Typical commercial available nuclear detectors for density measurement, based on the Caesium 662 keV peak, has a circular area with a radius of 2" and lower. For dual energy systems (x-ray and γ-ray) as described in U.S. Pat. Nos. 5,135,684 and 6,097,786, the area is normally even smaller due to the need for a composite window in the pipe in order to allow radiation from the low energy x-ray radiation to go through the pipe. The cover area in a 2" pipe with a typical commercially available γ-ray densitometer is typically 70-80% of the total cross sectional area of the pipe. However, when used in a 6" pipe, it is difficult to achieve more than 30% coverage of the cross section of the pipe. One way to increase the coverage is to place the density measurement inside a venturi passage as in U.S. Pat. No. 5,135,684. However, placing the nuclear density measurement inside a venturi passage also increases the amount of annular flow in the measurement section. When the source and detector is placed in the middle of the pipe, a too low density will be measured at annular flow. The error in the measurement will increase as the area of the pipe is increased. One way to compensate for this effect is to place the densitometer off-centre. However, the measurement errors due to gas concentration in the middle of the pipe would still be significant.

Yet another way to minimise the effect of annular flow is to use a mixing device. U.S. Pat. No. Re. 36,597 describes a method where a positive displacement meter is used to both measure the total flow rate and homogenise the multiphase mixture in advance of the composition measurement. Annular flow is then minimised; however, the multiphase meter becomes highly intrusive and fragile since it depends on a mechanical restricting or rotating device located in the multiphase stream. The repeatability of the measurement over time would also be vulnerable to sand erosion. Another way to reduce the presence of annular flow is to use a mixer. U.S. Pat. No. 5,135,684 refer to a method where a hold up-tank is used to homogenise the multiphase flow. However, the structure is highly intrusive, thus creating a pressure drop and hence limiting the production capabilities from the wells. The performance of the mixer would also be dependent on the flow rate and pattern such as length of gas and liquid slugs and could therefore limit the operational envelope of such a multiphase meter. Another method based on mixing of the multiphase flow is described in U.S. Pat. No. 6,272,934.

Yet another way to reduce the effect of annular flow is to perform the composition measurement at the cross section of an annular venturi is shown in WO00/45133, FIG. 1. However, this method is also intrusive and the repeatability of the measurement over time would also be vulnerable to sand erosion.

Also known are multiphase composition and flow meters based on microwaves. U.S. Pat. No. 4,458,524 discloses a multiphase flow meter that measures the permittivity (dielectric constant), density, temperature and pressure. Such a device uses phase shift between two receiving antennas to determine the permittivity.

Other techniques are further known being based on resonance frequency measurement. Examples of such techniques are disclosed in WO 03/034051 and U.S. Pat. No. 6,466,035. Techniques based on resonance frequency measurements are normally limited to multiphase conditions where the loss inside the pipe is small and would therefore normally not work for high water cut applications and saline water due to the high dielectric loss of the mixture. U.S. Pat. No. 5,103,181 describes a method based on measurement of constructive and destructive interference patterns in the pipe.

Also known are multiphase flow meters based on determination of permittivity of the multiphase mixture using capacitance and inductance sensors. Examples of such methods can be found in WO 00/45133 and NO 304333. These devises utilise a lower frequency for measurements of permittivity compared to RF and microwave based systems, and are therefore much more sensitive to changes in the water salinity and droplet size of the multiphase flow. By using a lower frequency it is also difficult to design a single measurement unit capable of performing cross sectional measurements at both oil and water continuous flow conditions and any droplet size since the relative impedance of oil and water continuous flow differs by many orders of magnitude at low frequency. Capacitance and inductance based flowmeters are also more prone to measurement drift problems since the sensor and electrodes are a part of an electronic circuit. The parameters of the electronic circuit are measured by comparing them to reference values which need to be stable within a few picofarads in order to obtain the required accuracy. Such stability is difficult to achieve because of signal line capacitance drift, temperature drifts and stray capacitances in the system related to such as buildup of solids or oil/water film on the pipe walls.

However, none of the above mentioned techniques are both non-intrusive and capable of performing accurate measurements of the flow rates at annular flow conditions or when the gas concentration is higher in the middle of the pipe. Thus, the main purpose of the present invention is to provide a method for accurate measurements of the flow rate of the individual components of a multiphase mixture at any flow regime, including annular flow and severe gas concentration in the middle of the pipe, without using a mechanical mixing or flow-conditioning device.

It is a purpose of this invention to provide a method for identifying gas concentration in the middle of the pipe and to further compensate permittivity and density measurements for the measurement error related to the degree of annular flow.

It is further a purpose of this invention to provide an improved apparatus to avoid the above mentioned limitations of the performance of presently known techniques for multiphase flow measurements.

It is still further a purpose of this invention to provide a single low-cost structure for performing accurate measurement of oil, water and gas flow rates.

And, it is a purpose of this invention to provide an almost non intrusive structure for performing the measurements without the need for an upstream mixing device.

The method according to the present invention comprises the following steps:
  a. electromagnetic loss and phase measurements are performed in at least two directions of the pipe,
  b. the degree of annular flow is determined based on the measurements of step a,
  c. the permittivity of the flow mixture is calculated based on the results from steps a and b including correction for the degree of annular flow,
  d. the mixture density is measured and compensated for the degree of annular flow,
  e. the temperature and pressure are obtained,
  f. the velocity of liquid and gas are determined, and g. based on the knowledge of densities and permittivities of the components of the fluid mixture, and the result from the above steps a-f, the volume and mass flow rates of the gas and liquid or liquids of the fluid mixture are calculated.

The flow meter according to the invention is further characterized by the features as defined in the independent apparatus claim.

Dependent claims define preferred embodiments of the invention.

The invention will be further described in the following, by way of example, with reference to the figures, where:

BRIEF DESCRIPTION OF THE DRAWINGS

FIGS. 1a-1d show graphical representations of four examples of annular flow through a cross section of a 4" pipe, FIG. 2 shows a schematic longitudinal sectional view of a first flow meter according to the invention, FIG. 5 shows phase difference as a function of frequency at low loss for the flow meter of FIG. 2, FIGS. 6a and 6b show the electromagnetic field below the cut-off frequency $TE_{11}$ or at high loss inside a flow meter according to FIG. 2, FIGS. 7a and 7b show the electric field for the waveguide modes $TE_{11}$ and $TM_{01}$ in the cross section of a flow meter according to FIG. 2, FIG. 8 shows phase difference as a function of frequency at low loss for the flow meter of FIG. 2.

Figure 3:
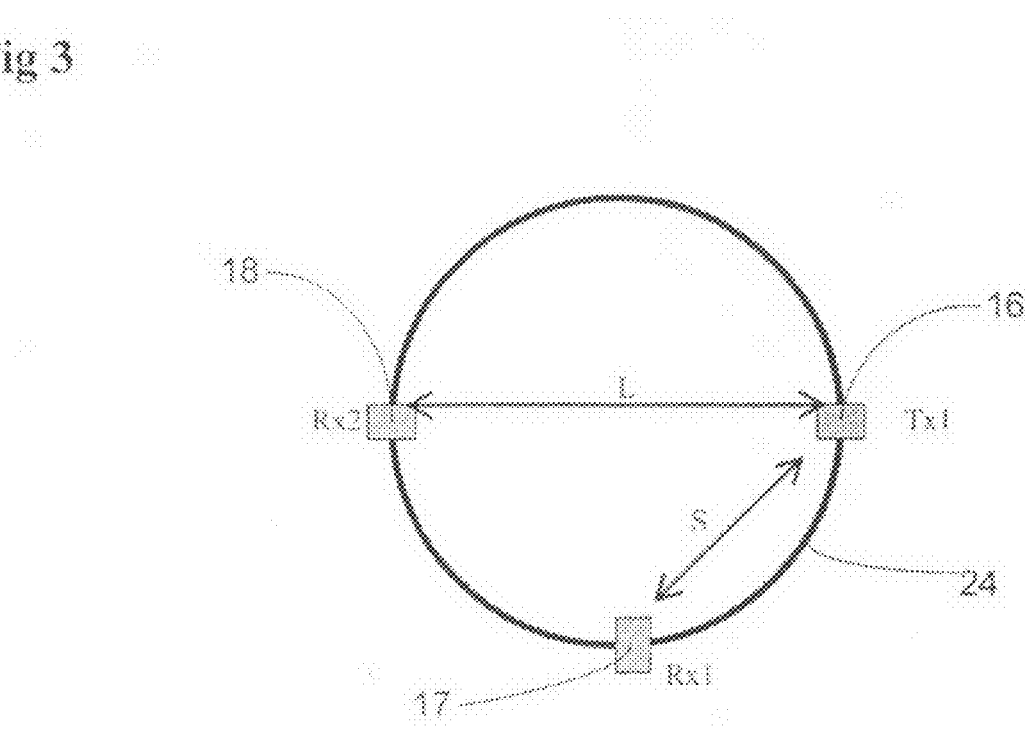
FIG. 3 shows a schematic cross sectional view along the line III-III in FIG. 2.

1) Measurements to determine the variation of gas concentration in the pipe cross-section, i.e. degree of annular flow.
2) Measurements of the flow components, e.g. oil, water and gas, in a cross section of the pipe. This includes measurement of permittivity, density and obtaining the temperature and pressure of the flow. The permittivity and density measurements are compensated for the variation of gas concentration in the cross section of the pipe.
3) Measurements of liquid and gas velocity. By combining the measurements from points 2) and 3) above and knowing the cross-sectional area of the pipe (sensor) and the density of oil, water and gas—it is possible to calculate the oil, water and gas volumetric and mass based flow rates The weakness of existing multiphase meters is mainly related to two factors, namely that:

1) Existing multiphase meters rely on a homogenous mixture between oil, water and gas in the cross section of the pipe. At large variation of gas concentration in the pipe cross-section, great measurement errors will occur. In FIG. 1 is shown a graphical representation of the effect on the GVF (% Gas) measurement with a typical gamma densitometer based on a 2" detector 1 and a gamma source 34 for four examples of annular flow where all the gas 37 is in the middle of the pipe and all the liquid 38 is distributed along the pipe wall. Although this is an extreme case since all the gas is concentrated in the middle of the pipe, it illustrates that large errors will occur in the measurements.
2) Need of using a mechanical mixing element. Some multiphase meters use a mechanical mixing device to homogenise the multiphase flow. A mixer would reduce the amount of annular flow; however, it makes the meter highly intrusive. Some of the mixers may also contain moving mechanical objects that are vulnerable to sand erosion and could even be damaged by fast variations in the velocity associated with start up of a well.

The uniqueness of the present invention is the ability to detect presence and degree of annular flow and compensate the measurement error related to the degree of annular flow.

Figure 4:
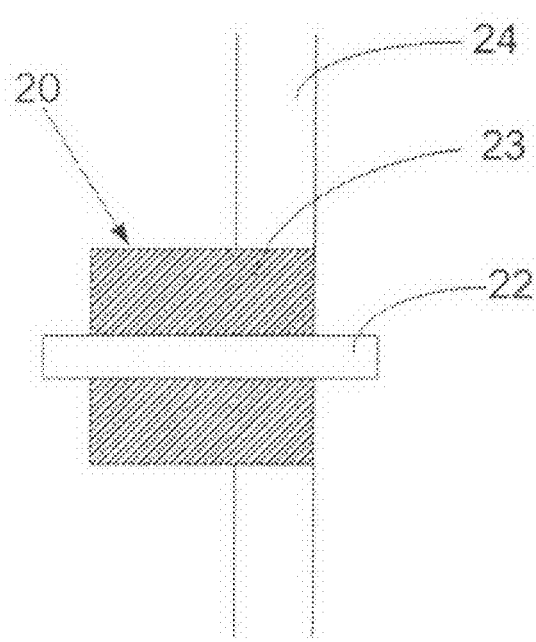
FIG. 4 is a sketch at a larger scale of a detail of FIG. 2.

The attached FIG. 2 illustrates a flow meter according to the invention. The antennas 16, 17, 18, 19, 20 and 21, as can be seen in more detail in FIG. 4, are in effect coaxial conductors that are inserted into the pipe designed such that the centre conducting wire 22 which is isolated from the pipe wall 24 by a dielectric material 23 such as plastic or ceramic. Three of the antennas are in this example used as transmitters, and are therefore given prefix a Tx, and three of the antennas are used as receivers and are therefore given a prefix Rx. The direction of the flow is illustrated by an arrow 25. A densitometer 29 is also a part of the flow meter. An electronic system capable of transmitting and receiving a broadband signal (typical 10 Mhz-4,0 Ghz) on the various antennas, a computer and devices for measurement of temperature and pressure are also parts of the flow meter. But for simplicity, these devices are omitted from all the figures and the further discussion since it will be clear to the skilled person how they may be implemented. The pipe arrangement of FIG. 2 may also be referred to as a sensor in the context of this patent application.

Loss and phase measurements are performed by measuring the received power and phase difference of a broad band signal (typical 10 Mhz-4,0 Ghz) which is transmitted from a sending antenna and received at two receiving antennas located at a different length from the sending antenna. The measurement is done at at least two and preferable three planes in the pipe where one plane is at the cross section, a second is the longitudinal direction and a third at an angle (such as 45 degrees) to the flow direction. The frequency is typically varied from 10 Mhz until 4,0 Ghz depending on the pipe diameter. By recording the frequency at at least three predetermined phase differences and using a calibration constant for the system, the permittivity within the pipe can be measured in all directions. Based on the measurements of the permittivity in the various directions, the degree of annular flow can be measured and compensated for by using a mathematical model such as neural networks since the various measurements are differently affected by concentration of gas in the middle of the pipe.

FIG. 5 shows the phase vs. frequency measurement of a flow meter according to FIG. 2 at high loss inside the pipe. When the loss inside the pipe is high, the electromagnetic field will behave according to plane wave theory. When the flow is well mixed, the phase vs. frequency curve 4 is more or less linear as shown in FIG. 5. When gas is concentrated in the middle of the pipe, the curve 5 is more non-linear. Hence, by analysing the distribution of the phase measurements, annular flow can also be detected and compensated for. One way to develop a mathematical model describing the behaviour of this feature is to use empirical data and train a neural network to detect annular flow and compensate the measurement. The network could be trained to predict the corresponding well mixed permittivity or measurement frequency, where well mixed permittivity or frequency in this context means the theoretical permittivity or frequency that would have been measured in an equivalent homogeneous multiphase mixture.

Laboratory tests based on this method has provided 100% identification of annular flow, and large reduction in measurement errors due to annular flow.

When the pipe acts as a wave guide (low loss), the permittivity is measured by measuring a frequency related to the cut-off frequency for some of the wave-guide modes of the pipe. The distribution of the electric and magnetic field within a pipe is frequency dependent. Table 8.9, on page 425 of Fields and Waves in Communication Electronics written by S. Ramo, J. R Whinnery and T. V. Duzer (John Wiely & Sons, 1964, second edition) shows the electric and 25 magnetic field lines and the corresponding cut-off frequencies for the various TM and TE classes of waves (waveguide modes) of a circular pipe. FIG. 6 shows the electromagnetic field inside a flow meter according to FIG. 2 at high loss or at a frequency well below the cut-off frequency $TE_{11}$ of the pipe. Below the lowest cut-off frequency of the pipe, which is $TE_{11}$, the electromagnetic field will propagate according to plane wave theory as illustrated by the arrows 6 in the FIG. 6. FIG. 7 shows the electric field lines of the two lowest wave-guide modes of a circular wave-guide, namely $TE_{11}$ 7 and $TM_{01}$ 8. When the electric field (E-field) in the pipe changes from plane wave propagation into $TE_{11}$, a step occurs in the phase difference 9 of the receiving antennas as shown in FIG. 8. By applying a frequency sweep on the transmitter and measuring the frequency at at least three predetermined phase differences, the frequency of the phase step, which is a measure of the cut-off frequency $TE_{11}$ of the pipe, can be calculated.

Figure 13:
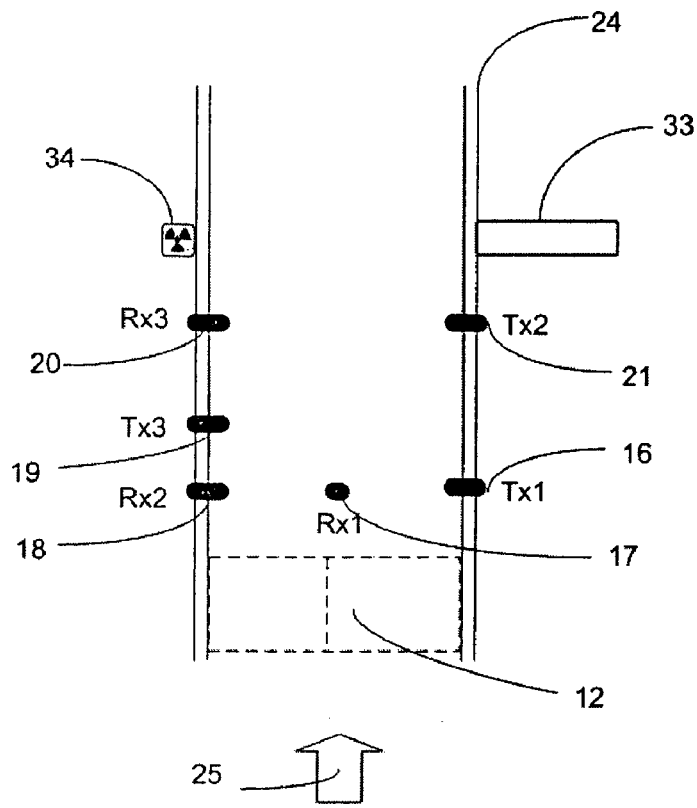
FIG. 13 shows a second embodiment of a flow meter according to the invention.

A measurement of the permittivity within the pipe performed in the longitudinal direction of the pipe can be obtained by placing a microwave reflector 12, such as a cross or fin with a length of approximately 0.5 pipe diameters, at a predetermined distance from the transmitting antenna. Such an arrangement is shown in FIG. 13 where a microwave reflector 12 is placed upstream the transmitting antenna Tx3 19.

Figure 15:
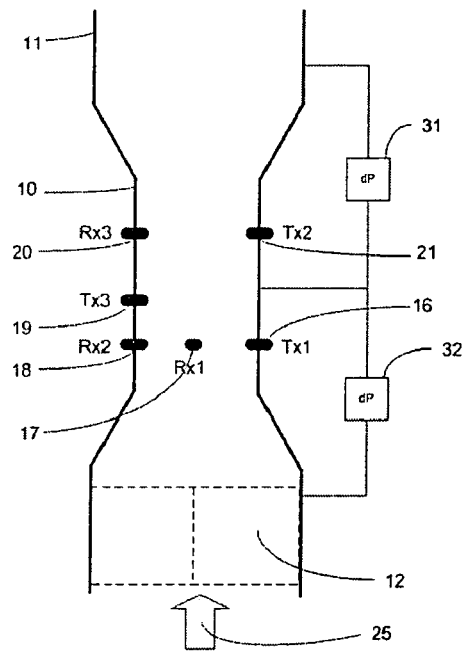
FIG. 15 shows a fourth embodiment of a flow meter according to the invention.

FIG. 8 shows the measured phase difference vs. frequency for the sensor arrangement of FIG. 15 at low loss. The frequency location of the phase change 9 corresponds to the cut-off frequency of the wave-guide mode $TE_{11}$ of the venturi throat 10. The frequency location of the phase change 13 of FIG. 8 corresponds to the first half-wave reflection between the transmitting antenna Tx3 19 and the reflector 12, which is above the cut-off frequency $TE_{11}$ of the large pipe 11 and is a function of the permittivity inside the pipe. Similarly, the phase change 15 corresponds to the frequency of the first half-wave reflection between the transmitting antenna Tx3 19 and the reflector 12 which is above the cut-off frequency $TM_{01}$ of the large pipe 11. The frequency locations of the phase shifts 9, 13 and 15 are also a function of the permittivity within the pipe. Hence, by measuring the frequency location of the phase shifts 9, 13 and 15 and using a calibration constant for the system, three measurements of the permittivity within the pipe can be obtained. $TE_{11}$ 7 and $TM_{01}$ 8 have different E-field distributions in the cross section of the pipe as shown in FIG. 7. Since one measurement is performed in the cross section and two measurements are performed in the longitudinally direction based on the waveguide modes $TE_{11}$ and $TM_{01}$, the three measurements are differently affected by an inhomogeneous mixture in the cross section of the pipe, such as gas concentration in the middle of the pipe (annular flow). The measurements can be obtained by performing a frequency sweep on Tx1 16 and measuring the frequency at at least three predetermined phase differences on Rx1 17 and Rx2 18. The frequency location of these phase shifts are used as a starting point for a second and third frequency sweep transmitting on Tx3 19 and recording the phase between Rx3 20 and Rx2 18. First, the frequency is further increased recording the frequency at at least three pre-determined phase differences in order to identify the frequency location of the phase shift 15. Then the frequency is reduced while recording the frequency at at least three predetermined phase differences for identifying the frequency location of the phase shift 13. Based on the recorded frequencies for the phase shifts 9, 13 and 15 and using calibration constants for the system, the permittivity within the pipe can be measured. Based on these three measurements of the permittivity, the degree of annular flow can be calculated using a mathematical model such as neural networks since the three measurements are differently affected by the degree of annular flow. The model can be derived based on empirical data obtained by measuring the phase shifts 9, 13 and 15 for a wide range known degrees of annular flow. The calculated degree of annular flow is then used to compensate the permittivity and density measurement using an experimental derived mathematical model such as a neural network.

At low loss, the degree of annular flow can also be measured by selecting a measurement frequency that is well below the cut-off frequency $TE_{11}$ of the pipe and measuring the loss in two or more planes of the pipe. When using this method at low loss to measure the degree of annular flow, the reflector 12 can be omitted from the flow meter, making it less intrusive. Since the cut-off frequency of $TE_{11}$ 9 is a function of the permittivity of the multiphase mixture inside the pipe, the measurement frequency will vary as a function of the permittivity. At the measurement frequency, the pipe would not act as a wave guide and consequently the E-field will be as shown in 7 of FIG. 7. At a frequency that is well below the cut off frequency of $TE_{11}$, the E-field will propagate according to plane wave theory as shown in 6 of FIG. 6. The loss is measured by transmitting on the selected measurement frequency well below the cut-off frequency of $TE_{11}$ on antenna Tx1 16 of FIG. 2 and recording the received power on antenna Rx1 17 and antenna Rx2 18 of FIG. 2. Then, using the same frequency, the next step is transmitting on antenna Tx3 19 and receiving on antenna Rx2 18 and Rx3 20. A third plane can be obtained by transmitting on antenna Tx3 19 and receiving on antenna Rx2 18 and Rx1 17. Based on the measured loss in the two or three measurement planes, the degree of annular flow can be calculated using an experimentally derived mathematical model and used to compensate the permittivity and density measurements using a mathematical model such as a neural network.

Figure 9:
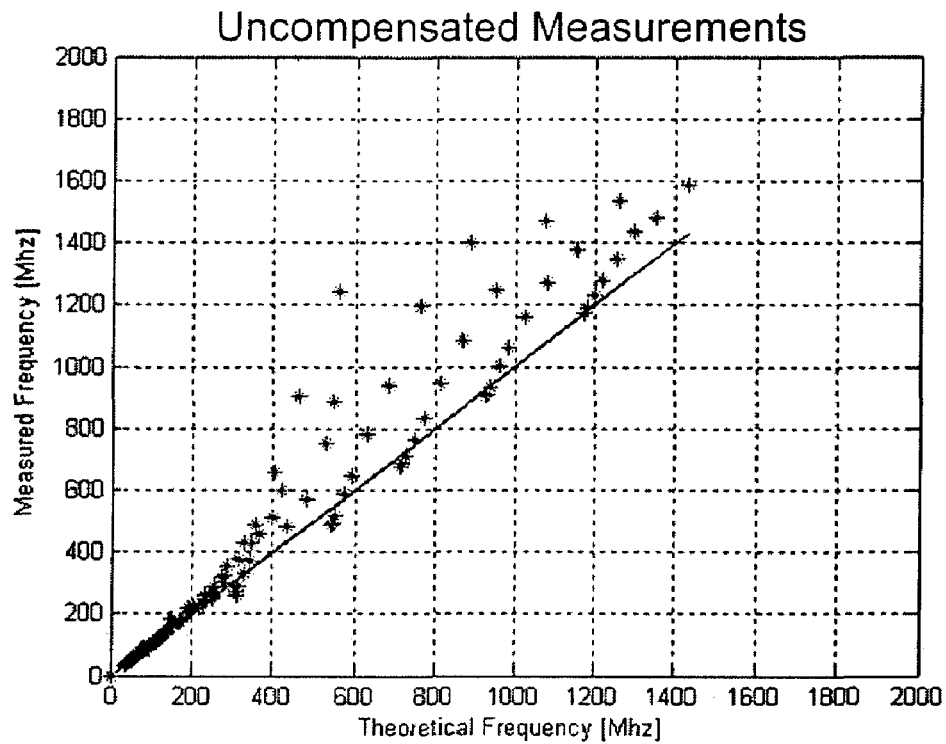
FIG. 9 shows the un-compensated frequency measurements for various liquids at pure annular flow for the flow meter of FIG. 2
Figure 10:
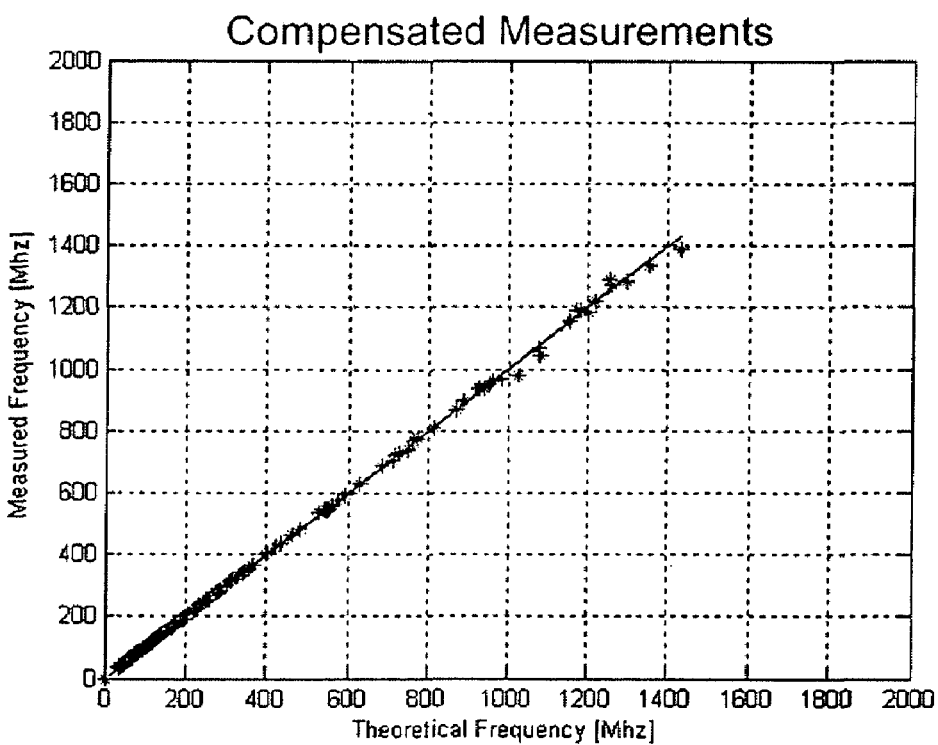
FIG. 10 shows measurements corresponding to FIG. 9, compensated for annular flow.
Figure 11:
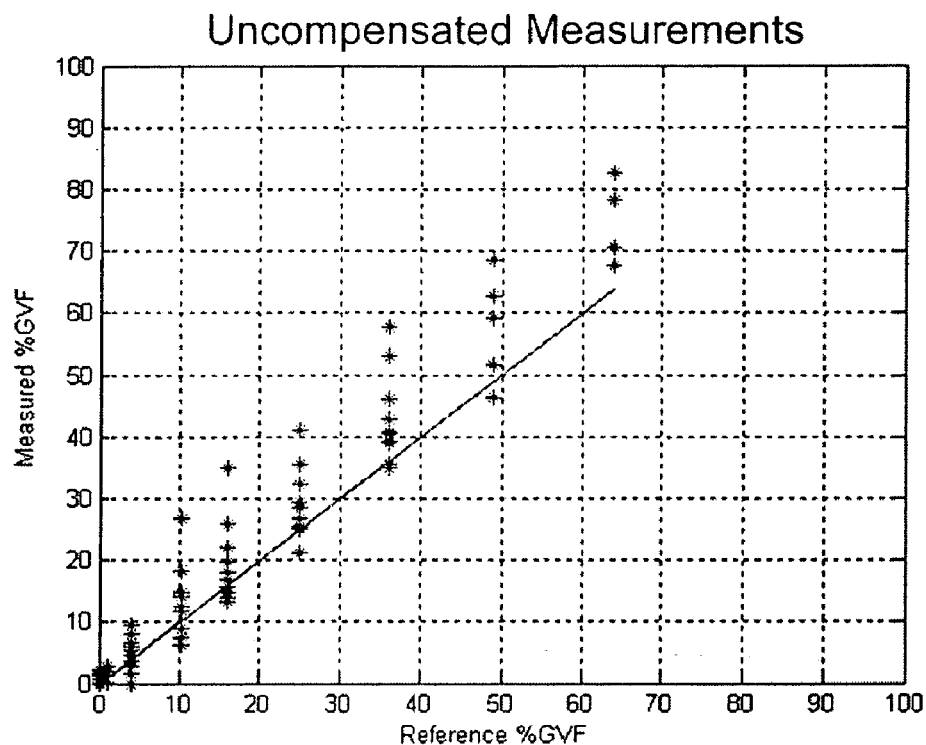
FIG. 11 shows the un-compensated GVF (% Gas) measurements for various liquids at pure annular flow.
Figure 12:
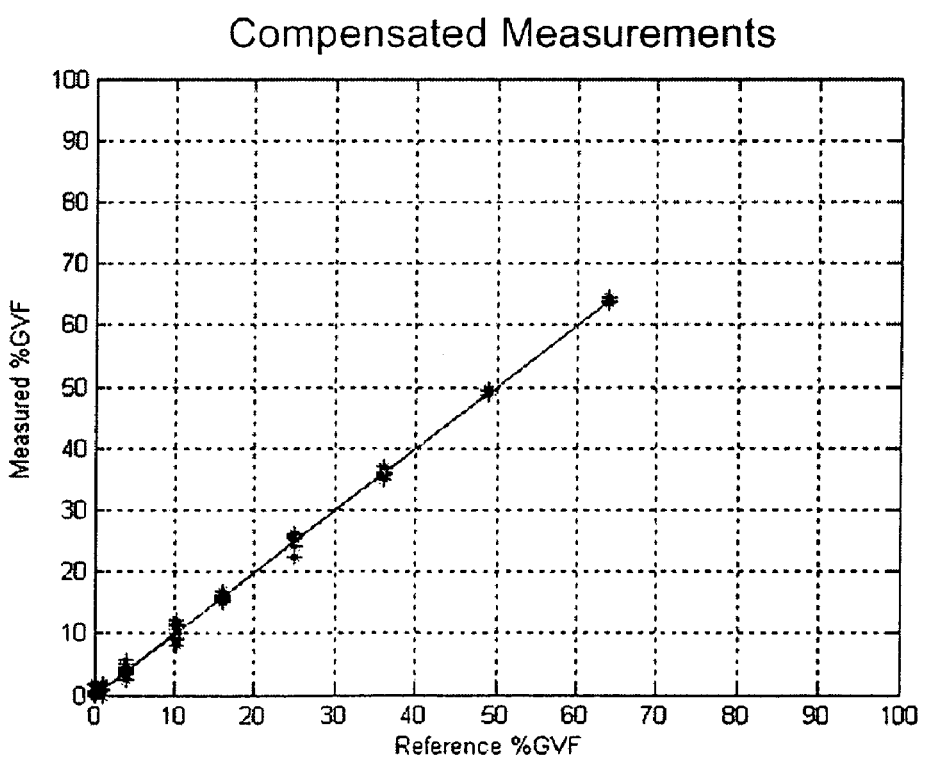
FIG. 12 shows measurements corresponding to FIG. 11, compensated for annular flow.

FIG. 9 shows the measured frequency vs. the theoretical frequency based on the cross sectional measurement plane for a gas void range (GVF) of 0-64% at a degree of annular flow of 1.0 and a wide range of liquids. The measured frequency is the average frequency of three different predetermined phase differences and the theoretical frequency in this context means the theoretical value that would have been measured in an equivalent homogeneous multiphase mixture where the degree of annular flow is 0.0. FIG. 10 shows the compensated frequency measurements based on the method described above using a neural network as the mathematical model for calculating the theoretical homogeneous frequency value. FIG. 11 shows the uncompensated GVF (% Gas) measurements for a GVF range from 0-64% at a degree of annular flow of 1.0 and a wide range of liquids. FIG. 12 shows the measurements of the GVF compensated for the degree of annular flow.

In order to calculate the oil, water and gas fractions in the cross section of the pipe, a measurement of the cross sectional density is also required. This measurement would also be affected by the degree of annular flow. Knowing the degree of annular flow in the pipe, the density measurement can be compensated for the effect on the measurements in a similar manner using an experimentally derived mathematical model, such as a neural network.

Figure 17:
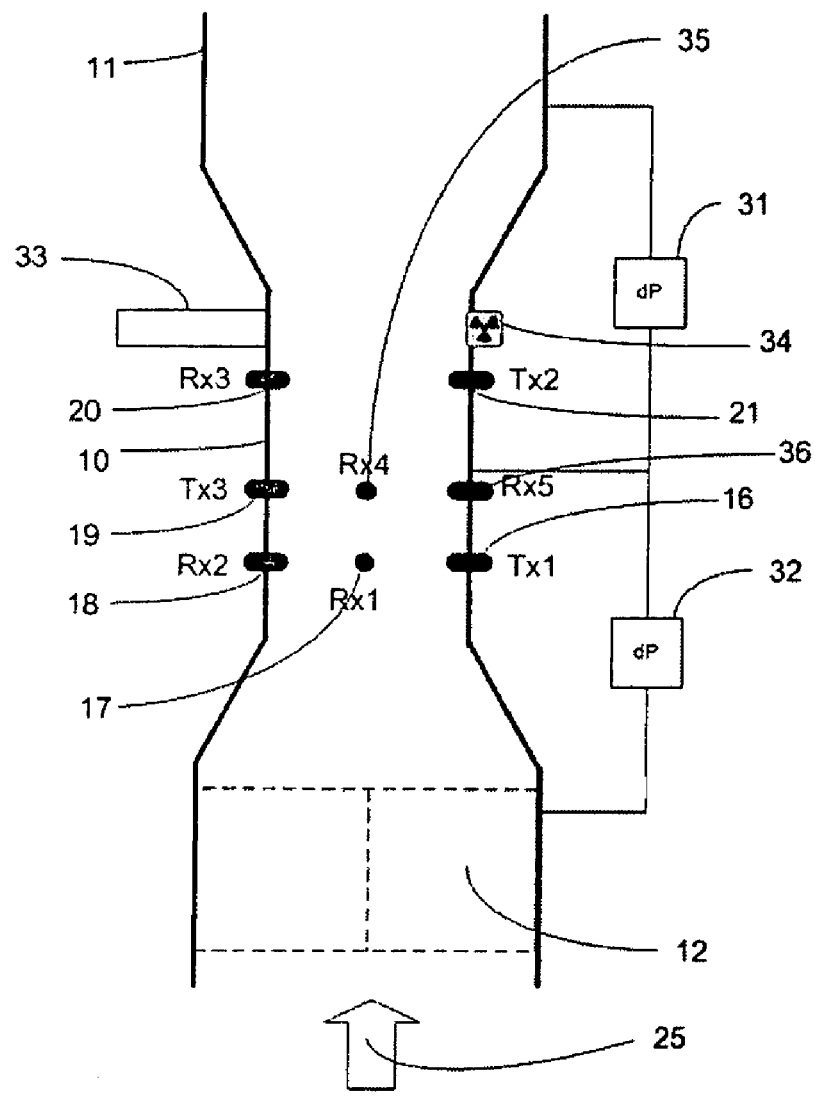
FIG. 17 shows a sixth embodiment of a flow meter according to the invention, The method according to the invention includes three main elements as follows.

The density measurement is, according to the invention, performed in two ways depending on the application:

1) Gamma ray absorption (FIGS. 13 and 17). By measuring the gamma ray absorption 33 of the multiphase mixture based on radiation from a gamma source 34 and knowing the absorption coefficient of oil, water and gas and the permittivity of the multiphase mixture and the permittivity of oil, water and gas, it is possible to calculate the mixture density in an iterative calculation. As a part of this iteration, the gamma ray absorption measurement can be corrected for the presence of annular flow by a mathematical model, such as a neural network.

Figure 14:
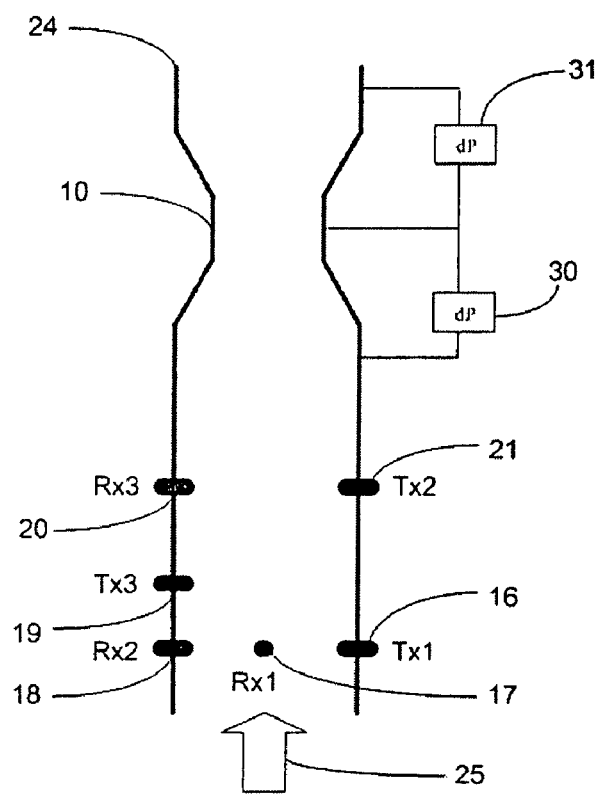
FIG. 14 shows a third embodiment of a flow meter according to the invention.

2) Venturi mass flow measurement (FIGS. 14 and 15). A venturi can be used to measure the density of the mixture. The pressure drop across the inlet of a venturi 30 is a function of the mass flow and density of the multiphase mixture. Furthermore, the pressure drop across the outlet of the venturi 31 is a function of the mass flow, density and compressibility of the multiphase mixture. Combining the pressure measurement of the inlet 30 and outlet 31 of the venturi, together with the measurement of the gas and liquid velocity from cross correlation (described in section below), it is possible to calculate the mixture density in an iterative fashion. However, at a degree of annular flow above 0, an error will be introduced to the density measurement. Then, as a part of the iteration, the measurement can be corrected for the degree of of annular.

Figure 16:
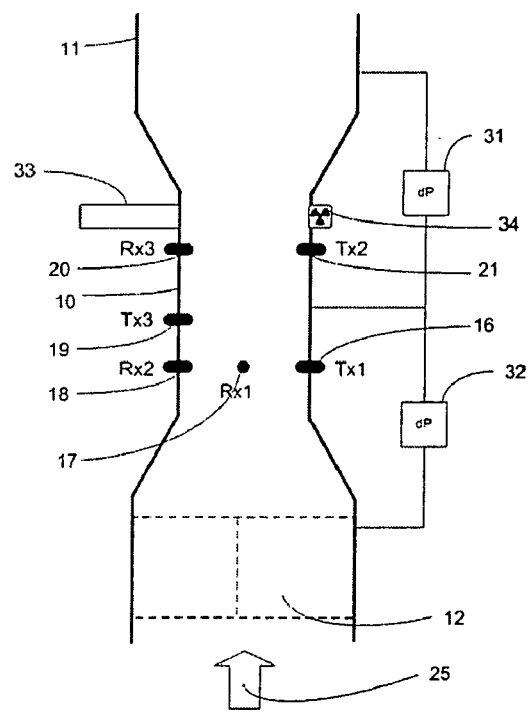
FIG. 16 shows a fifth embodiment of a flow meter according to the invention.

A combination of a gamma ray absorption (pt 1) and venturi (pt 2) measurements, e.g. as shown in FIGS. 16 and 17, may also be used. This combination can in some cases extend the operation envelope of the measurement system and enhance the measurement accuracy. In FIGS. 16 and 17 the gamma densitometer is placed inside the venturi throat together with the antennas such that the measurements can be performed under the same conditions. However, the gamma densitometer 33 and 34 may also be placed at either end of the sensor, but then it requires a compensation model to correct for the difference between the venturi throat 10 and pipe 11. This correction model can be derived based on empirical data. When the antennas are placed inside a venturi throat, the antennas 16, 17 and 18 has to be approximately 0.5 to 10 diameters from the start of the venturi throat; otherwise, the measurement of the cut-off frequency will be influenced by the diameter of the large pipe 11. Alternatively, in order to make the sensor more compact, the cross sectional measurement in such an arrangement can be placed more in the middle of the venturi throat, as shown in FIG. 17. Two additional antennas are now added to the venturi throat, namely Rx4 35 and Rx5 36. The cross sectional measurement can now be obtained by transmitting on Tx3 19 and receiving on Rx4 35 and Rx5 36.

The sensor is used to measure the composition and velocity (liquid and gas) of the multiphase mixture. Below is a more detailed description of the equations involved.

Velocity Measurement

By continuously transmitting and measuring the loss at the antenna pair Tx1 16/Rx2 18 and Tx221/Rx3 20 located at a known distance S+L 26, one can create two time varying signals that are shifted in time equal to the time it takes the multiphase flow to travel between the two antenna pairs. The measurement frequency is selected such that little energy is going in the longitudinal direction. At low loss the frequency would typical be substantially below the cut-off frequency $TE_{11}$ of the pipe. By cross correlating the two signals using the formula:

Equation 1:

$$R_{xy}(\tau) = \lim_{T \to \infty} \frac{1}{T} \int_0^T x(t-\tau) * y(t) dt$$

where x(t) and y(t) are the sampled signals, the time delay τ can be calculated. The time delay τ between the signals x(t) and y(t) is a measure of the time it takes a disturbance in the flow to go from the first to the second pair of antennas. Using high frequency signals to measure the flow disturbances also enables use of high sampling rates since it is possible to perform single measurements within a few micro seconds. Hence the signal contains information about small variations such as small gas bubbles in the liquid phase or water droplets in the oil phase or oil droplets in the water phase that typical represents the velocity of the liquid, and large variations such as gas slugs that represent the velocity of the gas phase. By applying the appropriate filtering of the sampled data and statistically sorting of the cross correlated velocities, it is possible to obtain a measure of both the liquid and gas velocity ($v_{liq}$ and $v_{gas}$).

Composition Measurement

However, in order to measure the flowrates of oil, water and gas, it is required to measure the cross sectional composition (% oil, % water & % gas) of the multiphase mixture of oil, water and gas. By measuring the mixture permittivity $\epsilon_{mix}$ and mixture density $\rho_{mix}$ the following equations can be used:

$$\Phi_{oil} + \Phi_{water} + \Phi_{gas} = 1 \quad \text{Equation 2:}$$

where:

$\Phi_{oil}$=Cross sectional volume fraction of oil
$\Phi_{water}$=Cross sectional volume fraction of water
$\Phi_{gas}$=Cross sectional volume fraction of gas $$\Phi_{oil} \times \rho_{oil} + \Phi_{water} \times \rho_{water} + \Phi_{gas} \times \rho_{gas} = \rho_{mix} \quad \text{Equation 3:}$$

where:

$\rho_{oil}$=Density of oil
$\rho_{water}$=Density of water
$\rho_{gas}$=Density of gas
$\rho_{mix}$=Measured density A temperature and pressure measurement is also required in order to compensate the above density parameters for temperature and pressure variations but, for simplicity, these will be omitted in the following discussions of the measurement principle.

The Bruggeman mixing equation relates the permittivity (dielectric constant) of a two component mixture to the volume fractions of the components. If the two component mixture is droplets as an inner phase dispersed in a continuous medium of an outer phase, the equation become:

Equation 4:

$$\frac{\varepsilon_{inner} - \varepsilon_{mix}}{\varepsilon_{inner} - \varepsilon_{outer}} * \left(\frac{\varepsilon_{outer}}{\varepsilon_{mix}}\right)^{\frac{1}{3}} = 1 - \frac{\Phi_{inner}}{\Phi_{inner} + \Phi_{outer}}$$

where:
$\varepsilon_{inner}$=Permittivity of the inner phase (dispersed phase)
$\varepsilon$hd outer=Permittivity of the outer phase (continuous phase)
$\varepsilon_{mix}$=Measured permittivity of the mixture
$\Phi_{inner}$=Volume fraction of inner phase (dispersed phase)
$\Phi_{outer}$=Volume fraction of outer phase (continuous phase)

A temperature and pressure measurement is also required in order to compensate the above permittivity parameters for temperature and pressure variations but, for simplicity, these will be ignored for the following discussions of the measurement principle.

The equation above can also be used for a three-phase mixture such as oil, water and gas in which the inner phase is a well mixed combination of two of the phases dispersed in an outer phase. E.g., an inner oil/water mixture may be dispersed in an outer continuous media of gas and similarly, gas bubbles may be dispersed in an outer continuous media of an oil/water mixture.

The lowest cut-off frequency of a circular wave guide, such as the pipe section of the flow meter, is $TE_{11}$ at:

Equation 5:

$$f_c = \frac{0.293}{r\sqrt{\mu\varepsilon}}$$

where:
$f_c$=Cut-off frequency
r=Radius of pipe
$\varepsilon$=Permittivity (dielectric constant) inside the wave guide (pipe)
$\mu$=Permeability inside the wave guide (pipe)

Below the cut-off frequency, the electric field 6 will propagate according to plane wave theory as illustrated in FIG. 6. At low loss in the pipe and above the cut-off frequency $f_c$ the electric field in the pipe is shown in 7 of FIG. 7 which correspond to $TE_{11}$. When the field in the pipe changes from plane wave propagation into $TE_{11}$, a step occurs in the phase difference of the receiving antennas Rx1 17 and Rx2 18 of FIG. 2. The phase step is illustrated in 9 of FIG. 8. By applying a frequency sweep on the transmitter Tx1 16 and measuring the frequency at at least three predetermined phase differences between the two receiving antennas, the frequency location (measured frequency) of the step change in the phase difference between the receiving antennas can be measured. Then, the measured frequency is a measure of the cut-off frequency $f_c$ of the pipe.

Equation 5 can be rearranged as:

Equation 6:

$$\varepsilon = \frac{k_2^2}{f_c^2}$$

where:

$$k_2 = \frac{0.293}{r\sqrt{\mu}}$$

$f_c$=Frequency of electromagnetic wave (cut-off frequency of $TE_{11}$)
$\varepsilon$=Permittivity (dielectric constant) inside the pipe hence $k_2$ can be determined by measuring the frequency $f_c$ with a known permittivity inside the pipe such as vacuum where the permittivity is 1,0.

The permittivity of the mixture at high loss inside the pipe (sensor) is measured by applying a frequency sweep to one of the transmitting antennas 16 or 19 and recording the frequency at at least three predetermined phase differences between two of the receiving antennas 17/18 or 18/20 located at a distance S and distance L from the transmitting antenna. Below the cut-off frequency or when the loss inside the pipe is large, the electric field will propagate according to plane wave theory. The phase difference between the two receiving antennas represents the wave travel time between the two points and can be written as:

Equation 7:

$$\Delta S = \lambda \frac{\Delta \theta}{2\pi}$$

where:
$\Delta S$=L-S (26)
$\Delta\theta$=Phase difference between receiving antennas
$\lambda$=Wavelength According to plane wave theory, the velocity of an electromagnetic wave can be expressed as:

Equation 8:

$$v = \lambda f = \frac{c}{\sqrt{\mu\varepsilon}}$$

where:
f=Frequency of electromagnetic wave
$\lambda$=Wavelength of electromagnetic wave
$\varepsilon$=Permittivity (dielectric constant) inside the pipe
$\mu$=Permeability inside the pipe
c=Speed of light Since the frequency is measured at predetermined phase difference, equation 6 and 7 can be combined giving:

Equation 9:

$$\varepsilon = \frac{k_1^2}{f^2}$$

where:

$$k_1 = \frac{c\Delta\theta}{\Delta S \sqrt{\mu}}$$

f=Frequency of electromagnetic wave $\varepsilon$=Permittivity (dielectric constant) inside the pipe $k_1$ can be determined by measuring the frequency at the phase difference $\Delta\theta$ with a known permittivity inside the pipe.

The permittivity within the pipe is measured in at least two directions. First, the transmitter is sending on Tx1 16 and receiving on Rx2 18 and Rx1 17 (FIG. 2) performing a measurement of the permittivity in the cross section of the pipe. Then the transmitter is sending on Tx3 19 and measuring on Rx2 18 and Rx3 20 performing a measurement of the permittivity in the longitudinal direction of the pipe. It is also possible to perform measurements of the permittivity by sending on Tx3 19 and receiving on Rx1 17 and Rx2 18 and hence performing a measurement that lies between the cross section and longitudinal measurements.

The effect of annular flow on various measurement directions may be explained as follows. When the flow is well mixed the phase-difference vs. frequency would be almost linear. If the flow is annular, which distorts the symmetry of the L and S path from the transmitter to the receivers, the phase difference would be much more curved. The longitudinal antennas (18, 19 and 20), as shown in FIG. 2, are less affected by annular flow since the symmetry is maintained also at annular flow.

By measuring the frequency at several predetermined phase differences, it is possible to both detect and compensate for the effect on the measurements. Experimental data has shown that the effect on the measurement is related to the slope ($d\theta/df$) of the phase difference. One way to compensate for the error introduced by annular flow is to first train a neural network to calculate the degree of annular flow. Then a second neural network could be trained to compensate for the error in the permittivity measurement related to the degree of annular flow.

The presence of annular flow can also be measured by measuring the loss in the longitudinal and cross-sectional direction. First, the transmitter is sending on Tx1 16 and receiving on Rx2 18 and Rx1 17, thus performing a measurement of the relative loss in the cross section of the pipe. Then the transmitter is sending on Tx3 19 and measuring on Rx2 18 and Rx3 20, performing a measurement of the relative loss in the longitudinal direction of the pipe. It is also possible to perform measurements by sending on Tx3 19 and receiving on Rx1 17 and Rx2 18 and hence performing a measurement that lies between the cross section and longitudinal measurements. At a degree of annular flow above 0, the longitudinal measurement would be different compared to the cross-sectional measurement. The measurement has to be made in such a way that the pipe does not act as a wave guide. One way to achieve this is by selecting a measurement frequency that is below the measured cut-off frequency for $TE_{11}$.

Yet another way to obtain measurement of the permittivity in the longitudinal direction of the pipe is to use a sensor arrangement as shown in FIG. 15 and described in the foregoing section. In this case the calibration constant k2 of equation 6 would be equal to the frequency location of the phase shift 13 and 15 of FIG. 8 with vacuum inside the pipe (sensor).

Measurement of gamma ray absorption is a widely used technique for density measurement. This technique takes into account that absorption of photon beam radiation in any material in the pipe (flow meter) can be expressed by the formula:

$$N = N_0 e^{-\mu \rho d} \qquad \text{Equation 10}$$

where:

$N_0$=Empty pipe count rate (radiation)

N=Measured count rate (radiation)

$\mu$=Radiation mass absorption coefficient of the material inside the pipe.

d=Transmission length of the radiation through the cross-section of the pipe $\rho$=Density of the material inside the pipe By measuring the count rate with a media inside the pipe with a known absorption coefficient such as fresh water, the parameter d can be determined according to equation 11:

Equation 11:

$$d = -\frac{\ln\left(\frac{N_{fresh\text{-}water}}{N_0}\right)}{\rho_{fresh\text{-}water} * \mu_{fresh\text{-}water}}$$

where:

$N_0$=Empty pipe count rate (radiation)

$N_{fresh\text{-}water}$=Measured count rate (radiation) in fresh water $\mu_{fresh\text{-}water}$=Radiation mass absorption coefficient of fresh water $\rho_{fresh\text{-}water}$=Density of fresh-water The density measurement does not cover the whole cross-sectional area of the pipe, consequently it relies on a homogeneous mixture in the cross section. The cover area in a 2" pipe with a typical commercial available $\gamma$-ray detector is typical 70-80% of the cross-section. However, when used in a 6" pipe, it is difficult to achieve more than 30% coverage of the pipe cross section. Nevertheless, knowing the degree of annular flow in the middle of the pipe, it is possible to compensate the measurement to provide a more correct measurement of the cross-sectional liquid and gas ratio. The compensation algorithm can either be derived from a geometrical description of the nuclear coverage area inside the pipe or by using an experimentally derived mathematical model, such as a neural network trained to correct the measurements.

Yet another way to measure the density is to use a venturi mass flow meter as shown in FIG. 14 and FIG. 15. Any restriction in the pipe will result in a change in the velocity of the multiphase mixture and introduce a pressure drop across the restriction. Based on the theory of fluid dynamics, the square root of the pressure drop 30 is proportional to the total mass flow rate in the pipe. A venturi tube is a structure where the pipe diameter is gradually reduced into a section of the pipe with a smaller diameter. The smaller section may be short or a relative long section. Then the diameter is gradually expanded to the original size of the pipe. Mass flow measurements with such a structure are described in ISO 5167-1 and ISO 5167-4.

According to ISO 5167-1, the mass flow rate can be calculated as:

Equation 12:

$$Qm = \frac{C}{\sqrt{1-\beta^4}} \frac{\pi}{4} d^2 \sqrt{2\rho\Delta p}$$

where:
Qm=Total mass flow rate
C=Discharge coefficient
β=Diameter ratio between venturi throat and pipe
d=Diameter of venturi throat
Δp=Measured pressure drop between inlet and venturi throat
ρ=Density of the multiphase mixture The pressure recovery at the outlet of the venturi will mainly depend on the mass flow rate, density, compressibility and viscosity of the multiphase fluid and the length and roughness of the venturi throat 10. When the gas content of the multiphase mixture is high, the pressure recovery at the outlet of the venturi will be greater compared to a multiphase mixture with low gas content. Hence, by combining equation 12 with a measurement of the pressure recovery at the outlet of the venturi 31, it is possible to obtain a measurement of the density of the multiphase mixture.

Equations 1-12, together with the correction functions, are typically solved in an iterative fashion to derive the oil, water and gas volumetric and mass based flow rates, using a computer as an integrated part of the flow meter.

Although several flow meters for measuring the flow rates of oil, water and gas have been described as examples for utilizing the present invention, the invention may also be used in other areas such as measurement of multiphase slurries with air or gas within the process industry, measurement of multiphase streams of coal and air or steam and water within the power generation industry. Furthermore, it will be clear to the skilled person that the invention is not limited to the embodiments described herein, but may be varied and modified within the frame of the invention defined by the features set forth in the appended claims and the equivalents thereof.

The invention claimed is:

1. A method for determining the flow rates of a fluid comprising a multi-component mixture of a gas and at least one liquid in a pipe, the method comprising the following steps:
    a. electromagnetic loss and phase measurements are performed in at least two directions of the pipe,
    b. the degree of annular flow is determined based on the measurements of step a,
    c. the permittivity of the mixture is calculated based on the results from steps a and b including correction for the degree of annular flow,
    d. the mixture density is measured and compensated for the degree of annular flow,
    e. the temperature and pressure of said mixture are obtained,
    f. the velocity of liquid and gas are determined, and
    g. based on the knowledge of densities and permittivities of the components of the fluid mixture, and the result from the above steps a-f, the volume and mass flow rates of the gas and liquid or liquids of the fluid mixture are calculated.

2. A method according to claim 1, wherein the composition of the flow mixture also is determined.

3. A method according to claim 1, wherein the electromagnetic measurements are performed in the cross sectional and longitudinal direction of the pipe.

4. A method according to claim 1, wherein said electromagnetic phase measurements are performed by doing a frequency sweep on a transmitting antenna in the flowing fluid and recording the frequency at at least three predetermined phase differences on two receiving antennas in the flowing fluid.

5. A method according to claim 4, wherein that in step b, the degree of annular flow is determined based on the distribution of the recorded frequencies.

6. A method according to claim 4, wherein that in step b, the degree of annular flow is determined based on the measured power difference on the receiving antennas.

7. A method according to claim 1, wherein that in step b, the degree of annular flow is determined based on at least two different measurements of the permittivity in the flowing fluid that are differently influenced by the degree of annular flow.

8. A method according to claim 1, wherein the liquid and gas velocity are measured by cross correlating measurements performed at two sets of antennas in the flowing fluid located at a known distance from each other.

9. A method according to claim 1, wherein the density of the fluid mixture is measured utilising γ-ray absorption techniques.

10. A method according to claim 1, wherein the density of the fluid mixture is measured using a venturi having an outlet.

11. A method according to claim 10, wherein the pressure recovery at the outlet of the venturi is measured.

12. A flow meter for determining the flow rates of a fluid comprising a multi-component mixture of a gas and at least one liquid in a pipe, the flow meter comprising a tubular section and the following elements:
    a. means for performing electromagnetic loss and phase measurements in at least two directions of the tubular section,
    b. means for determining the degree of annular flow based on the above measurements including a suitable data model,
    c. a computer having a storage element comprising a mathematical program for calculating the permittivity of the flow mixture based on the results from elements a and b above, including correction for the degree of annular flow,
    d. means for determining the mixture density and compensating the mixture density for the degree of annular flow,
    e. means for determining the velocity of liquid(s) and gas,
    f. means for determining the temperature and pressure of said mixture, and
    g. means for calculating the volume and mass flow rates of the gas and liquid or liquids of the fluid mixture based on the information from the elements a-f and knowledge of densities and permittivities of the components of the fluid mixture.

13. A flow meter according to claim 12, wherein the tubular section comprises one transmitting antenna and two receiving antennas located in the same cross section of the tubular section and one transmitting antenna and two receiving antennas spaced in the longitudinal direction of the tubular section.

14. A flow meter according to claim 13, comprising electronic means for transmitting a frequency sweep on one transmitting antenna at a time and recording phase difference and loss for the frequency sweep on two of the receiving antennas.

15. A flow meter according to claim 14, comprising means for calculating the degree of annular flow based on the recorded phase difference and/or electromagnetic loss.

16. A flow meter according to claim 14, comprising means for calculating the degree of annular flow based on permittivity measurements in the cross section and longitudinal direction of the tubular section.

17. A flow meter according to claim 13, comprising means for calculating the liquid and gas velocities by cross correlating measurements performed at two sets of antennas placed in different cross sections of the tubular section located a predetermined distance from each other.

18. A flow meter according to claim 17, comprising means for calculating the density of the fluid mixture based on measurement of pressure drop of a venturi having an outlet.

19. A flow meter according to claim 18, comprising means for measuring the pressure recovery at the outlet of the venturi.

20. A flow meter according to claim 12, comprising a device in the tubular section for reflecting electromagnetic waves in the longitudinal direction of the tubular section.

21. A flow meter according to claim 12, comprising a densitometer based on $\gamma$-ray absorption for measuring density of the fluid mixture.

* * * * *